US008972204B2

United States Patent
Kellaway et al.

(10) Patent No.: US 8,972,204 B2
(45) Date of Patent: Mar. 3, 2015

(54) GAS DISCRIMINATING SEMICONDUCTOR SENSORS

(75) Inventors: Mike Kellaway, Cambs (GB); John Andrew Johnston, Highfield Caldecote (GB)

(73) Assignee: Atmospheric Sensors Ltd., Little Therfor, Ely, Cambs (GB)

( * ) Notice: Subject to any disclaimer, the term of this patent is extended or adjusted under 35 U.S.C. 154(b) by 536 days.

(21) Appl. No.: 13/286,404

(22) Filed: Nov. 1, 2011

(65) Prior Publication Data

US 2014/0336952 A1    Nov. 13, 2014

Related U.S. Application Data

(60) Provisional application No. 61/456,108, filed on Nov. 1, 2010.

(51) Int. Cl.
| | | |
|---|---|---|
| G01N 27/00 | (2006.01) | |
| G01N 27/404 | (2006.01) | |
| G01N 27/12 | (2006.01) | |
| G01N 33/00 | (2006.01) | |

(52) U.S. Cl.
CPC ............ *G01N 27/404* (2013.01); *G01N 27/123* (2013.01); *G01N 33/0031* (2013.01)
USPC ........................................ 702/24; 73/31.06

(58) Field of Classification Search
CPC ............ F02D 41/1494; F02D 41/1456; G01N 27/4067; G01N 27/123; G01N 33/0031; G01N 27/404; H05B 1/0247
USPC ............ 702/24, 84, 99, 107; 73/23.35, 31.02, 73/31.05; 320/147; 422/90, 94, 98; 701/109
See application file for complete search history.

(56) References Cited

U.S. PATENT DOCUMENTS

| 4,847,783 A * | 7/1989 | Grace et al. ...................... 702/24 |
| 7,900,501 B2 * | 3/2011 | Moseley ...................... 73/31.02 |
| 2011/0077872 A1 * | 3/2011 | Loui et al. ...................... 702/24 |

* cited by examiner

*Primary Examiner* — John H Le
(74) *Attorney, Agent, or Firm* — James Creighton Wray

(57) ABSTRACT

Sensing particular gases in a mixture uses precise modulated heating. Sensor relative responses are compared at different temperatures and compared with known relative responses to identify gases and concentrations. Heater current sensors provide feedback control and microprocessor inputs. A processor controls complex impedances and varied frequencies in the sensors. Sensor responses at varied complex impedances and at varied frequencies are compared with known responses at those impedances and frequencies to determine existence and concentration of particular gases. Heater and sensor buses are separate or combined.

13 Claims, 1 Drawing Sheet

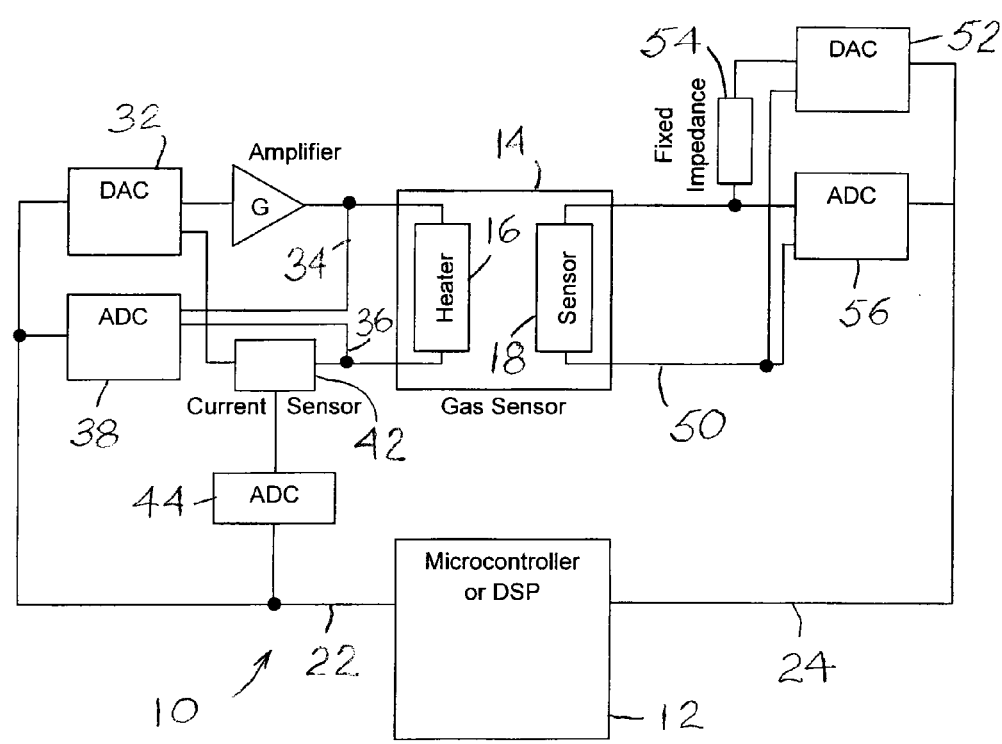

GAS DISCRIMINATING SEMICONDUCTOR SENSORS

SUMMARY OF THE INVENTION

This application claims the benefit of U.S. Provisional Application No. 61/456,108, filed Nov. 1, 2010, which is hereby incorporated by reference in its entirety as if fully set forth herein.

BACKGROUND OF THE INVENTION

Semiconductor gas sensors offer a low cost means of detecting gases with high sensitivity. However, they react to a number of gases and it is therefore difficult to discriminate between these in applications where more than one of these gases can be present.

The present invention addresses this problem in a number of ways used either singly or in combination and which can also significantly increase the sensitivity of the gas detection system in single gas applications.

The first of these is to use two or more semiconductor gas sensors of different characteristics, for example N type and P type sensors. Each sensor type responds differently to a particular gas, so one may estimate whether two or more gases are present by determining the relative response on each of the two or more sensors and comparing the relative response to the known relative responses to individual gases. To determine relative responses with maximum confidence, it is important to control the heater temperatures of each sensor precisely, as is done in the present invention.

The second technique is to scan or to modulate temperatures of the gas sensing elements over a wide temperature range and to detect the responses of the sensors at a number of carefully controlled temperatures. Semiconductor gas sensors respond to different gases in different ways across a range of temperatures. The response reaches a maximum value at a temperature that is characteristic for each gas. De-convolving the composite temperature response into the component for each constituent gas in a gas mixture thereby detects both the existence of different gases and their concentrations. The second technique can be combined with the first technique to further improve the results.

The third element of the approach is to use a modulated signal to measure the sensor response as a complex impedance, rather than the traditional resistance. This both improves the selectivity as determined by the other methods and allows a range of signal processing techniques to be used to improve noise rejection, and hence to increase effective sensitivity. A further improvement in the discrimination between gases in a mixture can be obtained by comparing the complex responses at a number of frequencies and comparing them with the known response to different gases.

SUMMARY OF THE INVENTION

In one implementation of the technique, a semiconductor gas sensor has a heater and a separate sensing element. The heater is used to bring the sensing element to its optimum operating temperature, which is preferentially carefully controlled. In this implementation the temperature is controlled by determination of the resistance of the heating element and by comparing the resistance with an expected value of resistance at the desired temperature. The expected resistance is determined from the heating element's known resistance at a calibration temperature and from the coefficient of resistance with temperature of the heating element material. A digital control loop is constructed that allows the temperature to be accurately controlled even in the presence of disturbing ambient heat flowing in and out of the sensor.

Once the sensor temperature is at its desired value, the complex impedance of the sensing element can be determined. In the present implementation this is done by exciting the sensor through a known reference impedance using a computer controlled Digital Analog Converter (DAC) and measuring the voltage across the sensing element using an analog to digital converter. By using various waveforms generated by the DAC and synchronizing the sampling of the voltage across the sensing element high-quality measurements of the complex impedance of the sensor are made.

Examples of the approaches are single or multiple frequency excitation and Discrete Fourier Transformation (DFT) of the results or broadband Pseudo Random Binary Sequence (PRBS) excitation with Fast Fourier Transformation (FFT) of the results. Other known signal processing techniques used in alternative applications may also be used.

By concentrating excitation and measurement at one or more frequencies, a significant reduction of the background noise is achieved leading to a greater usable sensitivity and permitting discrimination of the complex response to different gases to be used to determine the makeup of gas mixtures and to achieve selectivity.

In use the instrument is connected to a general purpose computer, which is used to further analyze and display the results of the measurement. Alternatively, a stand-alone instrument provides a display and user-interface functions.

Key Innovations of the invention include:
use of varied sensor excitation and synchronized measurements,
use of AC excitation and synchronized measurement to improve noise rejection and hence increase sensitivity,
use of two or more sensors having different characteristics to discriminate between different gases,
use of complex impedance in sensors as the measured quantity, increasing the potential discrimination between gases both through using real and imaginary parts and taking measurements at different frequencies, which provides selectivity,
measurement at a range of precisely controlled sensor temperatures as a means of discriminating between different gases, and
the ability to use other signal processing techniques such as signal averaging to both improve the quality of the measurement and to increase gas discrimination.

These and further and other objects and features of the invention are apparent in the disclosure, which includes the above and ongoing written specification, with the claims and the drawings.

BRIEF DESCRIPTION OF THE DRAWING

FIG. 1 schematically shows one example of an implementation of the invention.

DETAILED DESCRIPTION OF THE DRAWING

FIG. 1 schematically shows one example of an implementation of the invention.

The sensor system 10 shown in FIG. 1 employs a microcontroller or digital signal processor 12 and a gas sensor 14 having a heater 16 and a semiconductor gas sensor 18. Two or more sensors 14, preferably having different characteristics, may be used, but are not shown for clarity.

The drawings show one sensor for one system. Each sensor needs its own elements 32, 34, 36, 38, 42, 44, 50, 52, 54 and 56.

Buses 22 and 24 are connected to the processor 12. Busses 22 and 24 could be the same bus, or separate busses and elements 22, 24, 32, 38, 52 and 56 may be contained within the processor 12. The processor 12 precisely controls temperature and temperature variations of the heater 16 with a DAC 32 and an amplifier G. Heater voltage feedback lines 34 and 36 are connected to an ADC 38 to provide digital information of the applied heater voltage through the bus 22 to the processor 12.

Current sensor 42 senses current through the heater, and an ADC 44 provides digital feedback of that current to the processor 12.

A DAC 52 controlled by the processor 12 through bus 24 supplies power through a fixed impedance 54 across sensor circuit 50. Gas contacting the sensor 18 changes the impedance of the sensor 18 and hence voltage in the sensor circuit 50.

An ADC 56 provides digital signals of voltage in the sensor circuit through the bus 24 to the processor 12.

Many of the techniques (digital heater control, signal processing, averaging) give improved performance on a single sensor measuring a single gas.

While the invention has been described with reference to specific embodiments, modifications and variations of the invention may be constructed without departing from the scope of the invention, which is defined in the following claims.

We claim:

1. Apparatus comprising a gas sensor for sensing more than one gas having:
   a heater and a sensor,
   a heater control connected to the heater,
   a heater bus connected to the heater control,
   a sensor output connected to the sensor,
   an analog to digital converter connected to the sensor output,
   a sensor bus connected to the analog to digital converter connected to the sensor output,
   a processor connected to the sensor bus and to the heater bus,
   the processor adapted to control the heater through the heater bus and the heater control and adapted to receive digital signals from the sensor output through the sensor bus.

2. The apparatus of claim 1, wherein the heater control further comprises a heater resistance sensor and the processor further comprises a comparator comparing resistance of the heater with expected value of resistance at a desired heater temperature.

3. The apparatus of claim 2, wherein the heater control further comprises a control loop connected to the heater resistance sensor and to a heater input for fine controlling of heater temperature.

4. The apparatus of claim 2, wherein the heater resistance sensor is a heater current sensor connected to the heater and to the heater bus.

5. The apparatus of claim 1, wherein the heater control comprises a heater digital to analog converter connected to the heater control bus, a heater current sensor connected to the heater digital to analog converter, an amplifier connected to the heater digital to analog converter and to the heater, a heater analog to digital converter connected to the heater and to the heater control bus, and a current sensor analog to digital converter connected to the heater current sensor and to the heater control bus.

6. The apparatus of claim 1, wherein the sensor output further comprises a fixed impedance connected to the sensor and the digital to analog converter is connected to the fixed impedance, to the sensor and to the sensor bus.

7. The apparatus of claim 1, wherein the sensor output further comprises a fixed impedance connected to the sensor and a digital to analog converter connected to the fixed impedance, to the sensor and to the sensor bus and an analog to digital converter connected to the sensor and to the sensor bus.

8. The apparatus of claim 1, wherein the heater bus and the sensor bus are within a single combined heater and sensor bus.

9. The apparatus of claim 1, wherein the sensor comprises two or more sensors, including one or more P type sensors and one or more N type sensors, each with their associated control and monitoring circuits.

10. Apparatus comprising a gas sensor having:
    a heater and a sensor,
    a heater control connected to the heater,
    wherein the heater control further comprises a heater resistance sensor and a control loop connected to the heater resistance sensor and to a heater input for fine controlling of heater temperature,
    a sensor output connected to the sensor.

11. The apparatus of claim 10, wherein the heater control comprises a heater digital to analog converter connected to the heater control, a heater current sensor connected to the heater digital to analog converter, an amplifier connected to the heater digital to analog converter and to the heater, a heater analog to digital converter connected to the heater and to the heater control, and a current sensor analog to digital converter connected to the heater current sensor and to the heater control bus.

12. The apparatus of claim 10, further comprising a processor connected to the sensor output using signal processing techniques in a processor and improving quality of measurement and increasing gas discrimination.

13. The apparatus of claim 12, further comprising a processor connected to the sensor output using signal averaging in the processor and improving quality of measurement and increasing gas discrimination.

* * * * *